United States Patent [19]

Valkirs et al.

[11] Patent Number: 5,143,852
[45] Date of Patent: Sep. 1, 1992

[54] ANTIBODIES TO LIGAND ANALOGUES AND THEIR UTILITY IN LIGAND-RECEPTOR ASSAYS

[75] Inventors: Gunars E. Valkirs, Escondido; Kenneth F. Buechler, San Diego, both of Calif.

[73] Assignee: Biosite Diagnostics, Inc., San Diego, Calif.

[21] Appl. No.: 583,046

[22] Filed: Sep. 14, 1990

[51] Int. Cl.$^5$ ............... G01N 33/543; G01N 33/558; G01N 33/563; G01N 33/577

[52] U.S. Cl. .......................... 436/501; 435/6; 435/7.92; 435/7.93; 435/970; 436/512; 436/514; 436/518; 436/538; 436/540; 436/547; 436/548; 436/807; 436/822; 436/824; 530/413

[58] Field of Search ............... 435/6, 7.92, 970, 7.93; 436/501, 512, 514, 518, 548, 807, 817, 822, 824, 538, 540, 547; 530/413

[56] References Cited

U.S. PATENT DOCUMENTS

| | | | |
|---|---|---|---|
| 3,654,090 | 4/1972 | Schuurs et al. | 195/103.5 |
| 3,817,837 | 6/1974 | Rubenstein et al. | 195/103.5 |
| 3,878,187 | 4/1975 | Schneider et al. | 260/121 |
| 3,884,898 | 5/1975 | Schneider | 260/121 |
| 4,048,298 | 9/1977 | Niswender | 436/804 |
| 4,108,972 | 8/1978 | Dreyer | 424/1 |
| 4,200,690 | 4/1980 | Root et al. | 435/7 |
| 4,203,802 | 5/1980 | Rubenstein et al. | 435/188 |
| 4,233,402 | 11/1980 | Maggio et al. | 435/7 |
| 4,246,339 | 1/1981 | Cole et al. | 435/7 |
| 4,281,065 | 7/1981 | Lin et al. | 435/188 |
| 4,298,685 | 11/1981 | Parikh et al. | 435/7 |
| 4,366,241 | 12/1982 | Tom et al. | 435/7 |
| 4,391,904 | 7/1983 | Litman et al. | 435/7 |
| 4,425,438 | 1/1984 | Bauman et al. | 436/527 |
| 4,446,232 | 5/1984 | Liotta | 435/7 |
| 4,506,009 | 3/1985 | Lenhoff et al. | 435/7 |
| 4,552,839 | 11/1985 | Gould | 435/7 |
| 4,632,901 | 12/1986 | Valkirs et al. | 435/5 |
| 4,670,381 | 6/1987 | Frickey | 435/7 |
| 4,703,017 | 10/1987 | Campbell | 436/501 |
| 4,727,019 | 2/1988 | Valkirs et al. | 435/5 |
| 4,740,468 | 4/1988 | Weng et al. | 435/7 |
| 4,745,075 | 5/1988 | Hadfield | 436/523 |
| 4,775,636 | 10/1988 | Moeremans | 436/518 |
| 4,806,311 | 2/1989 | Greenquist | 422/56 |
| 4,959,307 | 9/1990 | Olson | 436/514 |
| 4,963,468 | 10/1990 | Olson | 436/578 |
| 5,037,764 | 8/1991 | Wilk et al. | 436/518 |

FOREIGN PATENT DOCUMENTS

| | | |
|---|---|---|
| 0200381 | 4/1986 | European Pat. Off. |
| 0271204 | 11/1987 | European Pat. Off. |
| 0378391 | 7/1990 | European Pat. Off. |
| 8500226 | 1/1985 | Int'l Pat. Institute |
| 8600668 | 10/1986 | PCT Int'l Appl. |

OTHER PUBLICATIONS

Rogers, et al. *Clin. Chem.* 24:95–100 (1976).

*Primary Examiner*—David Saunders
*Attorney, Agent, or Firm*—Lyon & Lyon

[57] ABSTRACT

Means for the detection of free ligand analogue conjugate in fluids from competitive ligand-receptor assay processes. Ligand analogue antibodies that bind the ligand analogue conjugate with substantially greater affinity than their affinity for target ligand are selected and used in competitive ligand-receptor assay processes to bind the free fraction of the ligand analogue conjugate. This means permits the detection of the free fraction of ligand analogue conjugate even in the presence of substantially higher concentrations of free target ligand. For the purposes of the present invention, ligand analogue antibodies are antibodies that exhibit at least 100× greater affinity for the ligand analogue conjugate compared to their affinity for the target ligand.

21 Claims, No Drawings

ANTIBODIES TO LIGAND ANALOGUES AND THEIR UTILITY IN LIGAND-RECEPTOR ASSAYS

FIELD OF THE INVENTION

This invention is in the field of ligand-receptor assays for the detection of selected target ligands in a fluid sample. More particularly, this invention relates to the use of antibodies specific for ligand analogues for the detection of ligand analogue conjugates in competitive ligand-receptor assays. The amount of ligand analogue conjugate that is detected through the use of such antibodies is related to the amount of the target ligand in a sample.

BACKGROUND OF THE INVENTION

As used herein, the term "ligand-receptor assay" refers to an assay for at least one target ligand which may be detected by the formation of a complex between the ligand and a receptor capable of specific interaction with that target ligand. The target ligand may be the analyte itself or a substance which, if detected, can be used to infer the presence of the analyte in a sample. In the context of the present invention, the term "ligand", includes haptens, hormones, peptides, proteins, deoxyribonucleic acid (DNA), ribonucleic acids (RNA), metabolites of the aforementioned materials and other substances of either natural or synthetic origin which may be of diagnostic interest and have a specific ligand receptor therefor. Ligand-receptor assays are generally useful for the in vitro determination of the presence and concentration of ligands in body fluids, food products, animal fluids, and environmental samples. For example, the determination of specific hormones, peptides, proteins, therapeutic drugs, and toxic drugs in human blood or urine has significantly improved the medical diagnosis of the human condition. There is a continuing need for simple, rapid assays for the qualitative, semi-quantitative, and quantitative determination of such ligands in a sample. Furthermore, in many situations, such assays need to be simple enough to be performed and interpreted by non-technical users.

Ligand-receptor assays rely on the binding of target ligands by ligand receptors to determine the concentrations of target ligands in a sample. Ligand-receptor assays can be described as either competitive or non-competitive. Non-competitive assays generally utilize ligand receptors in substantial excess over the concentration of target ligand to be determined in the assay. Sandwich assays, in which the target ligand is detected by binding to two ligand receptors, one ligand receptor labeled to permit detection and a second ligand receptor, frequently bound to a solid phase, to facilitate separation from unbound reagents, such as unbound labeled first ligand receptor, are examples of non-competitive assays. Competitive assays generally involve a sample suspected of containing target ligand, a ligand analogue conjugate, and the competition of these species for a limited number of binding sites provided by the ligand receptor. Those skilled in the art will appreciate that many variations of this basic competitive situation have been previously described and will not be discussed in detail herein except where pertinent to the general objectives of this invention.

Competitive ligand-receptor assays can be further described as being either homogeneous or heterogeneous. In homogeneous assays all of the reactants participating in the competition are mixed together and the quantity of target ligand is determined by its effect on the extent of binding between ligand receptor and ligand analogue conjugate. The signal observed is modulated by the extent of this binding and can be related to the amount of target ligand in the sample. U.S. Pat. No. 3,817,837 describes such a homogeneous, competitive ligand-receptor assay in which the ligand analogue conjugate is a ligand analogue-enzyme conjugate and the ligand receptor is capable of binding to either the target ligand or the ligand analogue. The binding of the antibody to the ligand analogue-enzyme conjugate decreases the activity of the enzyme relative to the activity observed when the enzyme is in the unbound state. Due to competition between unbound target ligand and ligand analogue-enzyme conjugate for ligand-receptor binding sites, as the target ligand concentration increases the amount of unbound ligand analogue-enzyme conjugate increases and thereby increases the observed signal. The product of the enzyme reaction may then be measured kinetically using a spectrophotometer.

Heterogeneous, competitive ligand-receptor assays require a separation of ligand analogue conjugate bound to ligand receptor from the free ligand analogue conjugate and measurements of either the bound or the free fractions. Methods for performing such assays are described in U.S. Pat. Nos. 3,654,090, 4,298,685, 4,425,438, and 4,506,009, European Patent Application 87309724.0, and PCT International Application No. PCT/US86/00668. Separation of the bound from the free may be accomplished by removal of the ligand receptor and anything bound to it from the free ligand analogue conjugate by immobilization of the ligand receptor on a solid phase or precipitation. The amount of the ligand analogue conjugate in the bound or the free fraction can then be determined and related to the concentration of the target ligand in the sample. Normally the bound fraction is in a convenient form, for example, on a solid phase, so that it can be washed, if necessary, to remove remaining unbound ligand analogue conjugate and the measurement of the bound ligand analogue conjugate or related products is facilitated. The free fraction is normally in a liquid form that is generally inconvenient for measurements. If multiple ligands are being determined in a single assay, the determination of the free fraction of ligand analogue conjugate for each ligand is made impossible if all are mixed in a single liquid unless the responses of the individual ligand analogue conjugates can be distinguished in some manner. However, detecting the free fraction of ligand analogue conjugate in assays that are visually interpreted is a distinct advantage because the density of the color developed in such assays is generally proportional to the ligand concentration over much of the range of ligand concentration.

One method that can be used to detect the free ligand analogue conjugate in a heterogeneous, competitive ligand-receptor assay process is to provide a second, immobilized receptor specific for the target ligand on a solid phase so that the ligand analogue conjugate not bound to the first ligand receptor can be bound to the second ligand receptor immobilized on the solid phase. A serious problem with this approach is that the concentration of target ligand in the sample is often several orders of magnitude larger than the concentration of ligand analogue conjugate used in the assay process. Under these circumstances, the target ligand and the ligand analogue conjugate compete for the available binding sites on the first ligand receptor resulting in essentially all of the ligand analogue conjugate being free in the assay fluid. When the assay fluid is contacted with the immobilized second receptor, the free target ligand and the free ligand analogue conjugate compete for binding sites provided by the second ligand receptor. The excess of free target ligand is such that its concentration remains several orders of magnitude larger than that of the free ligand analogue conjugate so that the second ligand receptor binding sites on the solid phase are substantially filled by the target ligand. The result of this assay process is that little or no signal may be observed on the solid phase when the concentration of the target ligand in the sample is high when in fact the assay should be designed to produce the maximum response for such concentrations of target ligand.

In European Patent Application No. 87309724.0, a method is described where the sample suspected of containing the target ligand and a ligand analogue conjugate are contacted with a bibulous strip that contains immobilized ligand receptor. When sufficient target ligand is present in the sample, free ligand analogue conjugate travels beyond the first immobilized ligand receptor zone and contacts a situs where either ligand receptor or another receptor capable of binding the ligand analogue conjugate is immobilized. If the receptor at the situs is receptor for the target ligand, then the problem of competition in the presence of high concentrations of target ligand exists as described above. Methods are described where the receptor at the situs is a receptor that binds to a species other than the ligand analogue on the free ligand analogue conjugate so that high concentrations of free target ligand do not compete for binding sites at the situs. The use of such receptors at the situs requires the development of additional ligand-receptor pairs for ligands unrelated to the target ligand for each target ligand to be assayed and restricts these assays to formats where the target ligand receptor is immobilized on a solid phase. Under these circumstances the assay of multiple target ligands in a single assay becomes complex and difficult to develop.

The method described in U.S. Pat. No. 4,506,009 utilizes a ligand analogue conjugate which has both the ligand analogue and an insolubilizing binding component coupled to the signal development element. An insolubilizing receptor is used to precipitate the free ligand analogue conjugate unless it is sterically hindered by the binding of the antibody specific for target ligand to the ligand analogue. This method overcomes some of the deficiencies of the prior art because it provides a method to determine the free fraction of ligand analogue conjugate without interference from the free target ligand, but it requires the coupling of two elements, the ligand analogue and the insolubilizing binding component, to the signal development element in such a way that the binding of the antibody to the ligand analogue sterically prevents the binding of the insolubilizing receptor to the insolubilizing binding component. The relative and absolute amounts of the ligand analogue and the insolubilizing binding component that are coupled to the signal development element must be empirically selected to achieve the desired result. The need for such manipulation is both time consuming and may limit the assay performance by restricting the ratio of ligand analogue per signal development element.

The present invention provides a method for the determination of the free fraction of ligand analogue conjugate in competitive ligand-receptor assays by utilizing antibodies that are specific for ligand analogue, the form of the ligand that is coupled to the signal development element. Such antibodies bind to the ligand analogue conjugate with substantially greater affinity than their affinity for the target ligand. We have discovered that such antibodies are produced as a result of the normal immune response to a ligand analogue coupled to an immunogenic carrier protein. Because no additional elements are incorporated into the ligand analogue conjugate and the selection of ligand analogue antibodies does not require additional antibody generation beyond that required to generate antibodies to the target ligand, the selection and utilization of ligand analogue antibodies provides a simple and effective means for the detection of free ligand analogue conjugate in competitive ligand-receptor assays, even in the presence of high concentrations of target ligand.

SUMMARY OF THE INVENTION

The present invention provides a means for the detection of free ligand analogue conjugate in fluids from competitive ligand-receptor assay processes. Ligand analogue antibodies that bind the ligand analogue conjugate with substantially greater affinity than their affinity for target ligand are selected and used in competitive ligand-receptor assay processes to bind the free fraction of the ligand analogue conjugate. This means permits the detection of the free fraction of ligand analogue conjugate even in the presence of substantially higher concentrations of free target ligand. For the purposes of the present invention, ligand analogue antibodies are antibodies that exhibit at least $100\times$ greater affinity for the ligand analogue conjugate compared to their affinity for the target ligand. Particularly preferred for practicing this invention are antibodies which exhibit at least $1000\times$ greater affinity. We have practiced this invention with antibody 21A3 with an affinity for ligand analogue conjugate almost $10,000\times$ greater for ligand analogue conjugate than for target ($7,427\times$). Preferred antibodies are monoclonal antibodies. We have discovered that ligand analogue antibodies that are monoclonal antibodies can be selected during the normal processes for generating monoclonal antibodies to the target ligand. Ligand analogue antibodies provide an effective means for the detection of free ligand analogue conjugate in competitive ligand-receptor assay processes without requiring the additional elements in the ligand analogue conjugate described by the prior art.

DETAILED DESCRIPTION OF THE INVENTION

The present invention provides a means for the detection of the free ligand analogue conjugate in fluids from competitive ligand-receptor assay processes. The detection of free ligand analogue conjugate in such fluids is accomplished by using antibodies that bind the ligand analogue conjugate with substantially higher affinity than their affinity for the target ligand so that the presence of target ligand at high concentrations does not significantly affect the binding of antibody to the free ligand analogue conjugate. For the purposes of the present invention, ligand analogue comprises a ligand that may be the target ligand or a chemical derivative of the target ligand and the linking arm that is used to couple the ligand to the signal development element or to an element coupled to the signal development element.

The ligand analogue antibody is selected on the basis of its binding affinity for ligand analogue conjugate relative to its binding affinity for target ligand. When target ligand, ligand analogue conjugate, and ligand analogue antibody are contacted such that target ligand and ligand analogue conjugate compete for binding sites provided by ligand analogue antibody, the binding reactions proceed according to the Law of Mass Action.

$$L + LAA = LAA{:}L \text{ and } LAC + LAA \rightleftharpoons LAA{:}LAC$$

At equilibrium, these two binding reactions are characterized by equilibrium constants (affinity constants) given by $$K_L = \frac{[LAA{:}L]}{[LAA][L]}$$

and $$K_{LAC} = \frac{[LAA{:}LAC]}{[LAA][LAC]}$$

where [LAA] is the concentration of free ligand analogue antibody, [L] is the concentration of free target ligand, [LAC] is the concentration of free ligand analogue conjugate, [LAA:L] is the concentration of bound target ligand, and [LAA:LAC] is the concentration of bound ligand analogue conjugate. The concentration of free ligand analogue antibody, [LAA], must be the same in both equilibrium expressions and by solving for [LAA] in one of the equations and substituting into the other equation the following relationship must be satisfied $$\frac{K_{LAC}}{K_L} = \frac{[LAA{:}LAC][L]}{[LAC][LAA{:}L]}$$

The ratio of the affinity constants for antibody binding to ligand analogue conjugate and to ligand is used to select ligand analogue antibodies for the purposes of this invention. Antibodies where the above ratio of affinity constants is greater than 100 are ligand analogue antibodies that can be used according to the present invention to detect free ligand analogue conjugate in competitive ligand-receptor assay processes in the presence of high concentrations of target ligand. The ratio of [LAA:LAC] to [LAC] is simply the ratio of the bound ligand analogue conjugate to the free ligand analogue conjugate, a variable that is easily measured. For example, after the equilibrium described above has been established, the ligand analogue conjugate bound to ligand analogue antibody can be separated by the double antibody method where an antibody is used to precipitate the ligand analogue antibody together with bound ligand analogue conjugate from the solution containing the free ligand analogue conjugate. Centrifugation or filtration of the precipitate effectively completes the separation process. The amount of ligand analogue conjugate can then be measured in the bound and the free fractions and the ratio is determined. In order to determine the ratio of the affinity constants, the quantity [L]/[LAA:L] must be determined. If excess antibody is used such that the total concentration of specific antibody binding sites is much greater than [LAA:LAC] and if the total concentration of target ligand is much greater than the total concentration of antibody binding sites, then [L] is approximately equal to the total concentration of target ligand and [LAA:L] is approximately equal to the total concentration of antibody binding sites. Given these desired conditions, one of ordinary skill in the art can determine the total concentrations of ligand and antibody, thereby determine the approximate value of [L]/[LAA:L], and using the measured value of the bound to free ratio, determine the ratio of the affinity constants. Those skilled in the art will appreciate that this measurement of the ratio of the affinity constants is performed under conditions that are similar to the conditions where the specific binding properties of ligand analogue antibodies are needed in order to bind ligand analogue conjugate in the presence of high concentrations of target ligand. In particular, the concentration of ligand analogue antibody should be in substantial excess over the concentration of the ligand analogue conjugate and the concentration of target ligand should be in substantial excess over the concentration of the ligand analogue antibody in the assay system.

The ligand analogue conjugate of the present invention comprises a ligand analogue coupled to a signal development element or to an element coupled to a signal development element. The ligand analogue of the present invention comprises a ligand that may be the target ligand or a chemical derivative of the target ligand and a linking arm that is used to couple the ligand to the signal development element or to an element that is coupled to the signal development element. Those skilled in the art will appreciate that the number of ligand analogues coupled to a signal development element can be adjusted to vary the affinity of a specific antibody for the ligand analogue conjugate. Methods for doing this are taught in EPO App. Ser. No. 90300283.0 (Pub. No. 0378,391). Preferred for use in the present invention are ligand analogue antibodies that bind the ligand analogue conjugate with substantially higher affinity than their affinity for the target ligand. Such antibodies may be classified into two groups. The first group comprises antibodies that bind the ligand analogue with substantially greater affinity than their affinity for the target ligand. The second group comprises antibodies that bind the ligand analogue conjugate with substantially greater affinity than their affinity for the target ligand or the ligand analogue. Antibodies in the second group are believed to bind to the ligand analogue conjugate by binding to the ligand analogue such that the binding is further stabilized by the proximity of the element linked to the ligand analogue and the juxtaposition of the chemical constituents thereon. The element to which the ligand analogue is coupled may be an element that does not contain the signal development element but rather is attached to the signal development element by covalent or non-covalent means. For example, the ligand analogue may be attached to a protein and the protein may be attached to the signal development element. The linking arm used to couple the ligand to the signal development element of the ligand analogue conjugate and to couple the ligand to a carrier protein, if necessary, to generate an immunogen can vary widely within the scope of this invention. Methods for the synthesis of immunogens using a variety of linking arms are known to those skilled in the art, see for example, U.S. Pat. Nos. 3,817,837, 3,878,187, 3,884,898, 4,203,802, and 4,281,065, and Rodgers, et al., Clinical Chemistry. 24, 95–100 (1976). One skilled in the art will appreciate that the choice of linking arm and the site on the ligand that is covalently coupled to the linking arm are dependent on the particular objectives of the assay.

Once ligand analogue antibodies have been selected that bind the ligand analogue conjugate with substantially higher affinity than their affinity for the target ligand, competitive ligand-receptor assays can be performed using these antibodies to detect free ligand analogue conjugate. Immobilization of the ligand analogue antibody on a solid phase provides a convenient format for contacting fluids from competitive ligand-receptor assay processes with the ligand analogue antibody and for washing the materials not bound to the solid phase away so that the ligand analogue conjugate bound to the solid phase can be detected. Alternatively, the ligand analogue antibody can be contacted in solution with the assay fluid and the fluid can then be contacted with an immobilized, solid-phase receptor for the ligand analogue antibody. The immobilized receptor, for example, can be the ligand analogue and can be used to bind ligand analogue antibody and any associated ligand analogue conjugate. Solid phases that are particularly preferred for the practice of this invention are solid supports onto which are immobilized antibodies in distinct loci capable of binding ligand analogue conjugates. In the context of the present invention, the term "immobilized" encompasses all physical mechanisms for immobilizing antibodies or receptors such that during the performance of the assay process, substantially all of the antibody or receptor remains in a pre-determined locus. Such mechanisms include covalent binding, non-covalent binding, chemical coupling, physical entrapment of particulates operatively associated with antibodies or receptors, and adsorption by hydrophobic/hydrophobic or hydrophilic/hydrophilic interactions. The immobilization of the antibody or receptor onto the solid support of the solid phase of the present invention may be accomplished in a number of ways. The antibody or receptor may be immobilized by the technique of entrapping antibody-coated or receptor-coated particulates by a porous matrix solid support. Methods for introducing said particulates to a porous matrix are discussed in U.S. Pat. Nos. 4,446,232, 4,740,468 and European Patent Application 86302521.9, incorporated by reference herein. A particularly preferred method of immobilization of the antibody or receptor onto the solid support wherein the solid support is a porous matrix comprises in part, immobilization of the antibody or receptor on the solid support by covalent or non-covalent chemical binding. Techniques for binding antibodies or receptors to a solid support are well known in the art. A variety of solid supports, including a porous matrix, a non-porous matrix, beads, membranes or filters, may be used in the present invention. Such solid supports can be incorporated into a variety of test devices including dipsticks and devices such as those described in U.S. Pat. Nos. 4,200,690, 4,246,339, 4,366,241, 4,632,901, and 4,727,019. A particularly preferred solid phase is a membrane suspended in a device such that when the assay fluid is contacted with the membrane, the fluid is of sufficient volume to completely fill the void volume of the exposed membrane such that the total surface area of the membrane and all antibody and receptor zones are contacted by the fluid. Such a device would also incorporate, if necessary, a means for removal of unbound ligand analogue conjugates from the membrane and a means for contacting the conjugates bound to immobilized ligand analogue antibodies on the membrane with materials needed to develop the signals associated with the signal development elements.

Clearly, the use of the method of the present invention with such devices would provide one with the ability to assay for multiple target ligands in a single sample using a single test device. In the multiple, simultaneous ligand-receptor assay formats a solid support comprising for each target ligand to be determined, at least one discrete reaction zone on which is localized either receptor specific for target ligand, receptor specific for ligand analogue antibody, or ligand analogue antibody.

Furthermore, the preferred solid phase as described above is particularly useful where it is highly desirable to simultaneously determine the presence of more than one target ligand of interest, such as for the determination of causative agents of a toxicological response. Accordingly the pattern of reactivity on the solid phase system, as determined by the presence of bound ligand analogue conjugates, provides an indication of the nature of the toxins eliciting the toxicological response.

Therefore, in one of the embodiments of the present invention, the assay fluid is contacted with a solid phase upon which is immobilized ligand analogue antibody. In a preferred embodiment the solid phase is composed of a non-diffusible bead, membrane or filter upon which the antibody is immobilized. In a particularly preferred embodiment, the solid phase is composed of a porous matrix upon which the antibody is immobilized. The antibody can be immobilized by a variety of methods including but not limited to direct covalent chemical attachment, indirect covalent chemical attachment, direct non-covalent chemical attachment, indirect non-covalent chemical attachment and physical entrapment.

The present invention is utilized in competitive ligand-receptor assay processes where sample fluid suspected of containing target ligand is contacted with fluids containing ligand analogue conjugate and ligand receptor in order to detect the presence or amount of the target ligand in the sample. Those skilled in the art will understand that the components that comprise the competitive assay process may be combined in many ways, for example, the sample may be contacted with the ligand receptor before, at the same time as, or after the contact of ligand analogue conjugate with ligand receptor. An incubation period is normally required so that the competitive binding reactions proceed such that the amount of free ligand analogue conjugate is related to the presence or amount of target ligand in the sample. For the purposes of this invention, "free" refers to ligand analogue conjugate that has ligand analogue binding sites that are not bound to the ligand receptor specific for the ligand and are capable of binding to the ligand analogue antibody when the assay fluid is contacted with a solid phase containing the ligand analogue antibody. When the ligand receptor binds with high affinity to the ligand analogue conjugate during the assay process, negligible dissociation of the ligand receptor/ligand analogue conjugate complex occurs during the contact of the assay fluid with the ligand analogue antibody immobilized on the solid phase. Under these circumstances, the amount of the ligand analogue conjugate that is bound to the ligand analogue antibody immobilized on the solid phase is related to the presence or amount of target ligand in the sample. However, if the dissociation of ligand receptor and ligand analogue conjugate is not negligible due to insufficient affinity, then the ligand receptor and complexes of the ligand receptor with target ligand or with ligand analogue conjugate may be removed from the assay fluid by several means. For example, the ligand receptor may be removed from the assay fluid by precipitation or by contact with a solid-phase receptor for the ligand receptor. Alternatively, the ligand receptor may be immobilized on a solid phase such as latex particles when first contacted with the liquid sample and centrifugation may be used to separate the free ligand analogue conjugate from that bound to the receptor. If such means are used to remove ligand receptor from the assay fluid prior to contacting the fluid with the immobilized ligand analogue antibody, then the "free" ligand analogue conjugate refers to ligand analogue conjugate that has no ligand receptor bound to it. The amount of ligand analogue conjugate that is bound to the ligand analogue antibody immobilized on the solid phase is related to the amount of target ligand in the sample.

Another competitive ligand-receptor assay method where the present invention can be effectively utilized are assays where the ligand receptor is immobilized on an immunochromatographic device such as the devices described in International Application No. PCT/US86/00668 and European Patent Application No. 87309724.0. In assays utilizing these devices, the sample fluid and the ligand analogue conjugate are contacted with the immobilized ligand receptor and the ligand analogue conjugate that passes beyond the zone of immobilized receptor is the free ligand analogue conjugate that is related to the presence or amount of ligand in the sample. By contacting the fluid containing free ligand analogue conjugate with a solid phase containing immobilized ligand analogue antibody, the free ligand analogue conjugate can be detected and related to the concentration of target ligand in the sample even in the presence of high concentrations of target ligand. In the assays of European Patent No. 87309724.0, a preferred use of the present invention is to immobilize the ligand analogue antibody at the situs for the binding of the ligand analogue conjugate not bound to the immobilized ligand receptor.

Following contact of the assay fluid with the immobilized ligand analogue antibody, the ligand analogue conjugate not bound to the ligand analogue conjugate on the solid phase may be removed by a washing process prior to the detection of the ligand analogue conjugate bound to the solid phase. In order to detect the ligand analogue conjugate bound to the solid phase, the signal development element of the ligand analogue conjugate must produce a detectable signal. Preferred signal development elements for use with the present invention are those which can produce a visual response that is used to detect the presence of the target ligand in the sample. Such signal development elements include sol particles that have strong absorbances in the visual spectrum such as colloidal gold, colloidal selenium, colored latex particles, and enzymes that produce colored products when contacted with appropriate substrates. Particularly preferred are enzyme channeling methods as described in U.S. Pat. No. 4,233,402 when used in conjunction with a solid phase as described in U.S. Pat. No. 4,391,904. Such methods substantially eliminate the need to provide a washing mechanism to remove ligand analogue conjugates not bound to the solid phase.

Ligand analogue antibodies may be selected from polyclonal preparations of antibody by employing affinity chromatography to select antibodies that bind ligand analogue with substantially greater affinity than their affinity for the target ligand. However, preferred antibodies are monoclonal antibodies specific for the ligand analogue. Methods for the generation of monoclonal antibodies are well known to those skilled in the art. The antibodies of the present invention include not only intact immunoglobulins but also fragments of immunoglobulins that are derived from intact immunoglobulins. It is also recognized that antibodies or fragments of antibodies can generated by genetic engineering methods from antibody gene sequences. Specific binding species that are produced by such methods that meet the selection criteria and are used according to the present invention are also considered to be antibodies in the context of the present invention. Exemplary methods for the selection of monoclonal ligand analogue antibodies are given in the following examples.

EXAMPLE 1

Synthesis of Acetylthiopropionic Acid

To a stirred solution of 3-mercaptopropionic acid (7 ml, 0.08 moles) and imidazole (5.4 g, 0.08 moles) in tetrahydrofuran (THF, 700 ml) was added dropwise over 15 minutes, under argon, a solution of 1-acetyl imidazole (9.6 g, 0.087 moles) in THF (100 ml). The solution was allowed to stir a further 3 hours at room temperature after which time the THF was removed in vacuo. The residue was treated with ice-cold water (18 ml) and the resulting solution acidified with ice-cold concentrated HCl (14.5 ml) to pH 1.5-2. The mixture was extracted with water (2×50 ml), dried over magnesium sulfate and evaporated. The residual crude yellow oily solid product (10.5 g) was recrystallized from chloroform-hexane to afford 4.8 g (41% yield) acetylthiopropionic acid as a white solid with a melting point of 44°-45° C.

Synthesis of p-Acetylthiopropionamide Benzoic Acid

Acetylthiopropionic acid (0.5 g, 0.0034 moles) was dissolved in anhydrous THF (3 ml). Carbonyldiimidazole (0.55 g, 0.0034 moles) was added and the mixture was stirred at room temperature for 45 minutes. A solution of p-aminobenzoic acid (0.46 g, 0.0034 moles) in anhydrous THF (2 ml) was added dropwise to the activated imidazolide while stirring and the reaction mixture was stirred for 2.5 hours at room temperature. The solvent was removed in vacuo and THF/water (7:4 ratio, 11 ml) was added to the residue to form a milky solution. The solution was warmed on a 50° C. water bath, water (300 ml) was added, and the mixture was stored at 4° C. overnight. The crystals were filtered and washed extensively with water and the product was dried in a vacuum desiccator. The recovered product (1.3 g) exhibited a melting point of 222°-224° C.

Synthesis of p-Acetylthiopropionamide Benzoylecgonine

To a stirred solution of p-acetylthiopropionamide benzoic acid (1.32 g, 0.0049 moles) in dry dimethylformamide (DMF, 8 ml) was added in one portion, under argon, carbonyldiimidazole (0.8 g, 0.0049 moles). The resulting solution was stirred at room temperature for 45 minutes and added in one portion, under argon, to a stirred solution of ecgonine hydrate (1.0 g, 0.0049 moles) in dry DMF (34 ml) containing 21% sodium ethoxide in ethanol (183 ul, 0.0049 moles). The solution was heated at 60°-65° C. for 6 hours after which time the DMF was removed in vacuo. The residual oil was subjected to chromatography on a 5×25 cm VYDAC RP C18 column using a linear gradient of 30 mM potassium phosphate, pH 4.6, to methanol to afford 0.53 g (19 % yield) of p-acetylthiopropionamide benzoylecgonine phosphate salt as a colorless foam.

Preparation of Benzoylecgonine Ligand Analogue Attached to Keyhole Limpet Hemocyanin (KLH), Bovine Serum Albumin (BSA), and Alkaline Phosphatase (AP The attachment of benzoylecgonine ligand analogue to proteins is achieved by reacting the free thiol, generated by hydrolysis of the p-acetylthiopropionamide benzoylecgonine, to proteins which contain a reactive maleimide that is the result of derivatization of the protein with succinimidyl 4-(N-maleimidomethyl)cyclohexane-1-carboxylate (SMCC, Pierce Chemical Co.). The free thiol form of the benzoylecgonine ligand analogue was generated by dissolving 30 mg of p-acetylthiopropionamide benzoylecgonine phosphate salt in 3.4 ml of 0.1 M potassium borate, pH 8.0. Sodium borohydride (29 mg) was added and after 15 minutes the thiol content was determined by the method of Ellman (Ellman, G. L., *Arch. Biochem. Biophys.*, 82, 70 (1959)) to be 15 mM. The pH of the solution was adjusted to 7.0 with glacial acetic acid prior to coupling to proteins.

KLH (6 ml of 14mg/ml) was reacted with sulfosuccinimidyl 4-(N-maleimidomethyl)cyclohexane-1-carboxylate (SULFO-SMCC by adding 15 mg of SULFO-SMCC and maintaining the pH between 7 and 7.5 with 1N potassium hydroxide over a period of one hour at room temperature while stirring. The protein was separated from the unreacted SULFO-SMCC by gel filtration chromatography in 0.1 M potassium phosphate, 0.02 M potassium borate, and 0.15 M sodium chloride, pH 7.0, and 24 ml of KLH-maleimide was collected at a concentration of 3.1 mg/ml. The free thiol containing benzoylecgonine ligand analogue (1.7 ml of 14 mM) was added to 6 ml of 3.1 mg/ml KLH-maleimide and the solution was stirred for 4 hours at 4° C. and then dialyzed against 3 volumes of one liter each of pyrogen-free phosphate-buffered saline, pH 7.4, prior to immunization.

BSA (3.5 ml of 20 mg/ml) was reacted with SMCC by adding a solution of 6.7 mg of SMCC in 0.3 ml acetonitrile and stirring the solution for one hour at room temperature while maintaining the pH between 7 and 7.5 with 1N potassium hydroxide. The protein was separated from unreacted materials by gel filtration chromatography in 0.1 M potassium phosphate, 0.02 M potassium borate, 0.15 M sodium chloride, pH 7.0. The free thiol form of the benzoylecgonine ligand analogue (0.17 ml of 14 mM) was added to the BSA-maleimide (2 ml at 8.2 mg/ml) and the solution was stirred for 4 hours at 4° C. The solution was used to coat microtiter plates for the detection of antibodies that bind the benzoylecgonine ligand analogue by standard techniques.

AP (1.5 ml of 10.9 mg/ml) was reacted with SULFO-SMCC by adding 3.1 mg of SULFO-SMCC to the solution and stirring at room temperature for one hour while maintaining the pH between 7.0 and 7.5 using 1 M potassium hydroxide. The protein was separated from the unreacted materials by gel filtration chromatography in 0.1 M potassium phosphate, 0.02 M potassium borate, 0.15 M sodium chloride, pH 7.0. The free thiol form of the benzoylecgonine ligand analogue (0.02 ml of 12 mM) was added to the AP-maleimide (0.2 ml at 3.56 mg/ml) and the solution was stirred for 1.5 hours at 4° C. The protein was separated from unreacted materials by gel filtration chromatography in 0.1 M potassium phosphate, 0.02 M potassium borate, 0.15 M sodium chloride, pH 7.0, and the benzoylecgonine ligand analogue conjugate was diluted for use in assays.

Benzoylecgonine ligand analogue was prepared by first reacting the N-hydroxysuccinimide of SULFO-SMCC with aminoethane sulfonic acid by dissolving 22.4 mg of SULFO-SMCC and 47.5 mg of aminoethane sulfonic acid in 5.16 ml of potassium borate, pH 7.46, and allowing the solution to stand for 10 minutes at room temperature. The protected thiol form, p-acetylthiopropionamide benzoylecgonine (5.8 mg) was dissolved in 0.54 ml of 0.12 M potassium carbonate, 0.6 mM EDTA in 40% methanol. After 8 minutes the thiol concentration was determined to be 19.7 mM by the method of Ellman. Potassium borate (0.2 ml of 0.5 M, pH 7.46) was added, mixed and 1.5 ml of the reaction mixture of SULFO-SMCC and aminoethane sulfonic acid was added and the pH was adjusted to 7.2 with 90 μl of 1N sodium hydroxide. Dilutions of this material were used as the benzoylecgonine ligand analogue in assays to determine the affinity of antibodies for the benzoylecgonine ligand analogue relative to the affinity of the antibodies for benzoylecgonine.

Preparation Of Latex-Immobilized Affinity-Purified Goat IgG Antibody Against The Fc Fragment Of Mouse IgG Affinity-purified goat-anti-mouse Fc (BiosPacific) and polystyrene latex particles (sulfated, 1.07 μm) (Interfacial Dynamics) were incubated separately at 45° C. for one hour, the antibody solution being buffered with 0.1 M 2-(N-morpholino) ethane sulfonic acid at pH 5.5. While vortexing the antibody solution, the suspension of latex particles was added to the antibody solution such that the final concentration of antibody was 0.3 mg/ml and the solution contained 1% latex solids. The suspension was incubated for 2 hours at 45° C. prior to centrifugation of the suspension to pellet the latex particles. The latex pellet was resuspended in 1% bovine serum albumin in phosphate-buffered-saline (PBS) and incubated for one hour at room temperature. Following centrifugation to pellet the latex, the pellet was washed three times by resuspension in PBS and centrifugation. The final pellet was resuspended in borate-buffered-saline, 0.1% sodium azide, pH 8.0, at a latex concentration of 1% solids. A 1% suspension of this latex preparation was capable of binding 40 μg/ml of monoclonal antibody.

Production and Primary Selection of Monoclonal Antibodies

Immunization of Balb/c mice was performed according to the method of Liu, D., Purssell, R., and Levy, J. G., Clin Chem, 25, 527–538 (1987). Fusions of spleen cells with SP2/0-Ag14 myeloma cells, propagation of hybridomas, and cloning were performed by standard techniques. Selection of hybridomas for further cloning began with culture supernatant at the 96-well stage. A standard ELISA procedure was performed with benzoylecgonine attached to BSA adsorbed to the ELISA plate. Typically, a single fusion was plated out in twenty plates and approximately 10–20 wells per plate were positive by the ELISA assay. At this stage, a secondary selection could be performed if antibodies to the SMCC part of the linking arm were to be eliminated from further consideration. An ELISA assay using BSA derivatized with SMCC but not containing the benzoylecgonine derivative identified which of the positive clones that bound the BSA-benzoylecgonine ligand analogue were actually binding the SMCC-BSA. Depending on the particular objectives for the antibodies obtained, the antibodies specific for SMCC-BSA may be eliminated at this step.

Assay for the Selection of Antibodies Binding Benzoylecgonine Ligand Analogue Conjugate with 100× Higher Affinity than their Affinity for Target Ligand Antibodies that are identified by the ELISA assay are subjected to further screening using the following assay method. Reaction mixtures containing 25 μl of an antibody dilution, 25 μl of diluent or a benzoylecgonine standard, and 25 μl of benzoylecgonine ligand analogue conjugated to alkaline phosphatase were incubated for 20 minutes at room temperature in V-bottom microtiter plates. A 25 μl volume of a 1% suspension of goat-antimouse IgG (Fc specific) adsorbed to latex was added to each reaction mixture and incubated another 10 minutes. The reaction mixtures were then subjected to centrifugation at 3000 rpm (1500 g) in a swinging bucket rotor. A 25 μl volume of the supernatant from each well was assayed for enzyme activity. By determining the enzyme activity in wells where high affinity antibody is in substantial excess over the amount needed to bind all of the immunoreactive conjugate, the enzyme activity that was associated with enzyme that did not contain bindable benzoylecgonine ligand analogue was determined. This non-immunoreactive fraction of the activity of the supernatant was subtracted from the measured activity to determine the activity associated with the immunoreactive fraction. Initially high affinity antibodies were selected in this assay by serially diluting the antibody in the range from approximately 100 nM to below one nM antibody concentration in the reaction mixture while using approximately one nM of benzoylecgonine ligand analogue conjugate. The free immunoreactive conjugate enzyme activity was determined by assaying the supernatant and the bound immunoreactive conjugate enzyme activity was determined by subtracting the free immunoreactive activity from the total immunoreactive conjugate enzyme activity. Under these conditions antibodies exhibiting a bound/free enzyme activity ratio of greater than 10 when the antibody is in excess over the conjugate are considered high affinity antibodies and are particularly preferred for the present invention.

In order to determine if the antibodies are benzoylecgonine ligand analogue antibodies, reaction mixtures were prepared for the assay as described where the antibody concentration that was used was in substantial excess over the concentration of antibody needed to bind substantially all of the conjugate as determined by the antibody dilution assay described above. In the examples described below, the concentration of antibody was approximately 30 nM, substantially higher than the concentration needed to bind substantially all of the conjugate. The reaction mixtures also contained benzoylecgonine or benzoylecgonine ligand analogue at concentrations that varied up to 32 μM, concentrations that are substantially higher than the total antibody binding site concentration. Such assay conditions can be used to determine the ratios of the affinities of the antibody for binding the benzoylecgonine ligand analogue conjugate and benzoylecgonine as well as the ratios of the affinities of the antibody for binding the benzoylecgonine ligand analogue conjugate and the benzoylecgonine ligand analogue by using the expression $$\frac{K_{LAC}}{K_L} = \frac{[LAA{:}LAC][L]}{[LAC][LAA{:}L]}$$

As described in the specification, [LAA:LAC]/[LAC] is the ratio of the bound immunoreactive enzyme activity to the free immunoreactive enzyme activity, [L] is approximated by the total ligand concentration, and [LAA:L] is approximated by the total antibody binding site concentration. The ratios of the affinities were determined for three antibodies that illustrate different species of ligand analogue antibodies using the assay conditions described and the above formula.

TABLE I

| Antibody | Ratio of Antibody Affinities Conjugate/ Benzoylecgonine | Ratio of Antibody Affinities Conjugate/ Benzoylecgonine Ligand Analogue |
|---|---|---|
| 11A3 | 102 | 53 |
| 21A3 | 7427 | 25 |
| 21B12 | 3770 | 1298 |

Antibody 11A3 just meets the requirement for being considered as a ligand analogue antibody (ratio of affinity for conjugate/ligand > 100) and exhibits similar affinities for benzoylecgonine ligand analogue and benzoylecgonine. Antibody 21A3 exhibits the properties of an antibody that has substantially higher affinity for the benzoylecgonine ligand analogue than its affinity for benzoylecgonine. Antibody 21B12 exhibits the properties of an antibody that has substantially higher affinity for the conjugate relative to either the benzoylecgonine ligand analogue or benzoylecgonine.

Use of Ligand Analogue Antibodies in a Competitive Assay Process for the Detection of Free Ligand Analogue Conjugate In order to test the effectiveness of the benzoylecgonine ligand analogue antibodies 11A3 and 21A3 for the detection of free benzoylecgonine ligand analogue conjugate in assays of samples containing benzoylecgonine, the antibodies were each immobilized on nylon membranes that were laminated to 20-mil thick polystyrene with a 4-mm diameter hole punched in the polystyrene so that the nylon membrane was exposed on both surfaces. The antibodies were applied to the nylon surface exposed by the hole in a 7 μl volume of solution containing 1.6 mg/ml antibody in 0.1 M citrate buffer at pH 3. After 10–15 minutes to allow the antibody to adsorb to the nylon, the remaining sites available for protein adsorption on the nylon were blocked by adding 7 μl of 1% casein in borate-buffered saline, pH 8.0, containing 10% sucrose. The membrane devices were stored at room temperature in a desiccator containing molecular sieve.

Assays were performed by preparing reaction mixtures in microtiter plate wells containing 40 μl of antibody 11A3 at 72 μg/ml, 40 μl of diluent or benzoylecgonine standard, and 40 μl of benzoylecgonine ligand analogue conjugated to alkaline phosphatase at 100 nM. The reaction mixtures were incubated for 30 minutes at room temperature prior to contacting 10 μl of the reaction mixture from one well with the nylon membrane containing one of the immobilized antibodies. After the reaction mixture fully wetted the nylon membrane exposed in the device, the membrane was contacted with an absorbent paper on one side and a wash solution (2×25 μl) containing borate-buffered saline, 0.05% LUBROL (Sigma), pH 8.0, was applied to the other side of the membrane to wash the unbound conjugate through the membrane and into the absorbent paper. Similarly, a substrate solution containing 10 mM 3-indoxyl phosphate was applied to the membrane (2×25 μl) to generate a blue color in the presence of bound conjugate. The second volume of substrate was applied without contact between the membrane and the absorbent paper so that the additional fluid prevented the membrane from drying out during the two-minute incubation period that followed. After the incubation was complete, the remaining substrate was washed out with borate-buffered saline to stop the development of color. The assay results were measured using a MINOLTA CR-241 by subtracting the background of a membrane that was not used in an assay from the measured response of the assay devices. The response is in units of delta E*. For a detailed explanation of this unit of measure for color, see *Color in Business, Science, and Industry* by D. B. Judd and G. Wyszecki, John Wiley and Sons. A response that is just visible above the background is approximately 3 delta E*. Twenty-five delta E* represents a dark blue color. The results of the assay are presented as the average of duplicates in Table II.

TABLE II

| [Benzoylecgonine] (μM) | Assay Response Using 11A3 on Membrane in Units of Delta E* | Assay Response Using 21A3 on Membrane in Units of Delta E* |
| --- | --- | --- |
| 0 | −1.7 | 0 |
| 0.1 | 0.8 | 0.6 |
| 0.32 | 7.3 | 5.3/ |
| 0.64 | 13.9 | 17.1 |
| 1.28 | 16.9 | 17.8 |
| 6.4 | 11.5 | 22.1 |
| 32 | 11.5 | 26.8 |
| 100 | 7.9 | 26.4 |
| 1000 | −1.4 | 21.6 |
| maximum# | 27.7 | 26.1 |

The maximum response is the response generated when only the conjugate and no antibody or ligand is present in the reaction mixture The results show that antibody 11A3 can be used to detect the presence of free conjugate in reaction mixtures containing up to 100 μM benzoylecgonine, a concentration that is 1000× higher than the concentration of conjugate in the reaction mixture.

Antibody such as 21A3 is particularly preferred for use the detection of free conjugate in the reaction mixtures containing high concentrations of benzoylecgonine. This antibody starts to exhibit effects due to the presence of benzoylecgonine only at 1000 μM, a concentration that is not achieved in physiological samples. It is our best mode antibody and Example 1 is the best mode for selection and use of this antibody in an assay.

Antibodies such as 21A3 are particularly preferred for use in quantitative assays because the assay response rises in relationship to the amount of ligand in the sample and does not fall below the maximum response for high ligand concentrations found in physiological samples. Using multiple standards to establish the assay response as a function of ligand concentration, the concentration of ligand in unknown samples can be determined. One skilled in the art will appreciate that this allows for fully quantitative assays.

We claim:

1. Method for determining the presence of at least one target ligand, capable of competing with a ligand analogue conjugate for binding sites available on a ligand receptor, said ligand analogue conjugate comprising at least one ligand analogue coupled to a signal development element, in a fluid sample suspected of containing said target ligand, comprising the steps of:
   a. contacting said fluid sample with a ligand receptor and a ligand analogue conjugate such that the amount of ligand analog ue conjugate that is not bound to ligand receptor is related to the concentration of the target ligand in the sample;
   b. contacting the fluid from step (a) with at least one ligand analogue antibody having a first affinity for said ligand analogue conjugate, and a second affinity for said target ligand, wherein said first affinity is at least 100 times greater than said second affinity, and said second affinity is greater than zero, wherein an amount of said ligand analogue conjugate not bound to ligand receptor is bound by ligand analogue antibody;
   c. contacting the fluid from step (b) with a receptor capable of binding to said ligand analogue antibody;
   d. removing ligand analogue antibody bound to said receptor from said fluid;
   e. measuring the amount of said ligand analogue conjugate bound to said ligand analogue antibody by developing a signal from said signal development element; and
   f. relating said measured amount of said ligand analogue conjugate to the presence or amount of said target ligand in said fluid sample.

2. Method for determining the presence of at least one target ligand, capable of competing with a ligand analogue conjugate for binding sites available on a ligand receptor, said ligand analogue conjugate comprising at least one ligand analogue coupled to a signal development element, in a fluid sample suspected of containing said target ligand, comprising the steps of:
   a. contacting said fluid sample with a ligand receptor and a ligand analogue conjugate such that the amount of ligand analog ue conjugate that is not bound to ligand receptor is related to the concentration of the target ligand in the sample;
   b. contacting the fluid from step (a) with at least one ligand analogue antibody having a first affinity for said ligand analogue conjugate, and a second affinity for said target ligand, wherein said first affinity if at least 100 times greater than said second affinity, and said second affinity; is greater than zero, wherein said ligand analogue antibody is immobilized on a solid phase wherein an amount of said ligand analogue conjugate not bound to ligand receptor is bound by ligand analogue antibody;
   c. measuring the amount of said ligand analogue conjugate bound to said ligand analogue antibody by developing a signal from said signal development element; and
   d. relating said measured amount of said ligand analogue conjugate to the presence or amount of said target ligand in said fluid sample.

3. Method for determining the presence of at least one target ligand, capable of completing with a ligand analogue conjugate for binding sites available on a ligand receptor, said ligand analogue conjugate comprising at least one ligand analogue coupled to a signal development element, in a fluid sample suspected of containing said target ligand, comprising the steps of:

a. at or before the commencement of the assay process, selecting at least one ligand analogue antibody specific for ligand analogue coupled to said signal development element, said ligand analogue antibody having a first affinity for said ligand analogue conjugate, and a second affinity for said target ligand, wherein said first affinity is at least 100 times greater than said second affinity, and said second affinity is greater than zero;
  b. contacting said fluid sample with a ligand receptor and a ligand analogue conjugate such that the amount of ligand analog ue conjugate that is not bound to ligand receptor is related to the concentration of the target ligand in the sample;
  c. contacting the fluid from step (b) with at least one ligand analogue antibody from step (a) wherein an amount of said ligand analogue conjugate not bound to ligand receptor is bound by ligand analogue antibody;
  d. contacting the fluid from step (c) with a receptor capable of binding to said ligand analogue antibody;
  e. removing ligand analogue bound to said receptor from said fluid;
  f. measuring the amount of said ligand analogue conjugate bound to said ligand analogue antibody by developing a signal from said signal development element; and
  g. relating said measured amount of said ligand analogue conjugate to the presence or amount of said target ligand in said fluid sample.

4. Method for determining the presence of at least one target ligand, capable of competing with a ligand analogue conjugate for binding sites available on a ligand receptor, said ligand analogue conjugate comprising at least one ligand analogue coupled to a signal development element, in a fluid sample suspected of containing said target ligand, comprising the steps of:

a. at or before the commencement of the assay process, selecting at least one ligand analogue antibody specific for ligand analogue coupled to said signal development element, said ligand analogue antibody having a first affinity for said ligand analogue conjugate, and a second affinity for said target ligand, wherein said first affinity is at least 100 times greater than said second affinity, and said second affinity is greater than zero;
  b. contacting said fluid sample with ligand analogue conjugate and ligand receptor such that the amount of ligand analogue conjugate that is not bound to ligand receptor is related to the concentration of the target ligand in the sample;
  c. contacting the fluid from step (b) with at least one ligand analogue antibody from step (a), said antibody immobilized on a solid phase, wherein an amount of said ligand analogue conjugate not bound to ligand receptor is bound by ligand analogue antibody;
  d. measuring the amount of said ligand analogue conjugate bound to said ligand analogue antibody by developing a signal from said signal development element; and
  e. relating said measured amount of said ligand analogue conjugate to the presence or amount of said target ligand in said fluid sample.

5. Method of claim 1 or 3 wherein said receptor is immobilized on a solid phase.

6. Method of claim 1 or 3 wherein said receptor is used to precipitate ligand analogue antibody.

7. Method of claim 1 or 2 wherein following step (a), the ligand receptor is removed from the fluid that is contacted with the ligand analogue antibody prior to such contact.

8. Method of claim 3 or 4 wherein following step (b), the ligand receptor is removed from the fluid that is contacted with the ligand analogue antibody prior to such contact.

9. Method of claim 7 wherein the ligand receptor is immobilized on a solid phase and the sample and ligand analogue conjugate fluids are contacted with the immobilized ligand receptor.

10. Method of claim 8 wherein the ligand receptor is immobilized on a solid phase and the sample and ligand analogue conjugate fluids are contacted with the immobilized ligand receptor.

11. Method of claim 1 or 2 or 3 or 4 wherein the ligand analogue antibody is a monoclonal antibody or monoclonal antibody fragment.

12. The method of claim 1 or 2 or 3 or 4 wherein said ligand analogue antibody has over 1,000 times the affinity for ligand analogue conjugate as it does for said target ligand.

13. The method of claim 1 or 2 or 3 or 4 wherein said ligand analogue antibody has over 10,000 times the affinity for ligand analogue conjugate as it does for said target ligand.

14. The method of claim 1 or 2 or 3 or 4 wherein said ligand analogue antibody is a polyclonal antibody, or antibody fragment.

15. The method of claim 14, wherein said antibody, or antibody fragment is selected by employing affinity chromatography to select antibodies that bind said ligand analogue conjugate with substantially greater affinity than their affinity for said target ligand.

16. The method of claim 1 or 2 or 3 or 4 wherein said target ligand is selected from the group consisting of haptens, polypeptides, DNA and RNA.

17. The method of claim 2 or 4 wherein at least two ligand analogue antibodies are immobilized onto said solid phase in at least two discrete zones so as to permit simultaneous detection of at least two target ligands.

18. Test devices for use with the method of claim 2 or 4 wherein said fluid sample and said ligand analogue conjugate are contacted with immobilized ligand receptor such that the ligand analogue conjugate that is not bound to said ligand receptor is contacted with a solid phase containing ligand analogue antibody specific for said ligand analogue conjugate.

19. Assay system for determining the presence or amount of at least one target ligand, capable of competing with a ligand analogue conjugate for binding sites available on a ligand receptor, said ligand analogue conjugate comprising at least one ligand analogue coupled to a signal development element, in a fluid sample suspected of containing said target ligand, said assay system comprising:

a. a ligand receptor;
  b. a ligand analogue conjugated to a signal development element;

c. at least one ligand analogue antibody, said ligand analogue antibody having a first affinity for said ligand analogue conjugate, and a second affinity for said target ligand, wherein said first affinity is at least 100 times greater than said second affinity, and said second affinity is greater than zero;

d. a receptor immobilized on a solid phase and capable of binding to said ligand analogue antibody.

20. Assay system for determining the presence or amount of at least one target ligand, capable of competing with a ligand analogue conjugate for binding sites available on a ligand receptor, said ligand analogue conjugate comprising at least one ligand analogue coupled to a signal development element, in a fluid sample suspected of containing said target ligand, said assay system comprising:

a. a ligand receptor;

b. a ligand analogue conjugated to a signal development element;

c. with at least one ligand analogue antibody immobilized on a solid phase, said ligand analogue antibody having a first affinity for said ligand analogue conjugate, and a second affinity for said target ligand, wherein said first affinity is at least 100 times greater than said second affinity, and said second affinity is greater than zero.

21. Method for determining the presence of at least one target ligand, capable of competing with a ligand analogue conjugate for binding sites available on a first ligand receptor, said ligand analogue conjugate comprising at least one ligand analogue coupled to a signal development element, in a fluid sample suspected of containing said target ligand, comprising the steps of:

a. contacting said fluid sample with said first ligand receptor and a ligand analogue conjugate such that the amount of ligand analogue conjugate that is not bound to said first ligand receptor is related to the concentration of the target ligand in the sample;

b. contacting said fluid sample with a second receptor immobilized on a solid phase, said second receptor capable of binding to said first ligand receptor and removing said first ligand receptor from said fluid sample prior to step (c);

c. contacting the fluid from step (b) with at least one ligand analogue antibody having a first affinity for said ligand analogue conjugate, and a second affinity for said target ligand, wherein said first affinity is at least 100 times greater than said second affinity, and said second affinity is greater than zero, wherein said ligand analogue antibody is immobilized on a solid phase wherein an amount of said ligand analogue conjugate not bound to said first ligand receptor is bound by ligand analogue antibody;

d. measuring the amount of said ligand analogue conjugate bound to said ligand analogue antibody by developing a signal from said signal development element; and e. relating said measured amount of said ligand analogue conjugate to the presence or amount of said target ligand in said fluid sample.

* * * * *